(12) United States Patent
Kolatkar et al.

(10) Patent No.: US 11,515,039 B2
(45) Date of Patent: Nov. 29, 2022

(54) SYSTEM AND METHOD FOR PREDICTING SURVIVAL TIME

(71) Applicant: UNIVERSITY OF SOUTHERN CALIFORNIA, Los Angeles, CA (US)

(72) Inventors: Anand Kolatkar, Los Angeles, CA (US); Peter Kuhn, Los Angeles, CA (US); Yan Liu, Los Angeles, CA (US); Paymaneh Malihi, Los Angeles, CA (US); Sanjay Purushotham, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 292 days.

(21) Appl. No.: 16/499,152

(22) PCT Filed: Apr. 27, 2018

(86) PCT No.: PCT/US2018/030013
§ 371 (c)(1),
(2) Date: Sep. 27, 2019

(87) PCT Pub. No.: WO2018/201083
PCT Pub. Date: Nov. 1, 2018

(65) Prior Publication Data
US 2021/0090732 A1 Mar. 25, 2021

Related U.S. Application Data

(60) Provisional application No. 62/491,893, filed on Apr. 28, 2017.

(51) Int. Cl.
*G16H 50/20* (2018.01)
*G16H 40/67* (2018.01)
(Continued)

(52) U.S. Cl.
CPC ............ *G16H 50/20* (2018.01); *G06N 3/04* (2013.01); *G06N 3/08* (2013.01); *G16H 10/40* (2018.01);
(Continued)

(58) Field of Classification Search
CPC ........ G16H 50/20; G16H 40/67; G16H 10/40; G16H 10/60; G16H 50/30; G16H 50/70;
(Continued)

(56) References Cited

U.S. PATENT DOCUMENTS 10,043,591 B1 * 8/2018 La ........................... G16H 10/65
10,282,588 B2 * 5/2019 Comaniciu ............ G06V 40/10
(Continued)

FOREIGN PATENT DOCUMENTS

JP   2006-202235   8/2006
JP   2013-529774   7/2013
(Continued)

OTHER PUBLICATIONS

A.J. Zurita "High Definition Single Cell Analysis (HD-SCA) of Prostate Cancer (PCA) Cells in Matched Bone Marrow and Blood from Patients", Annals of Onconlogy, vol. 25, Sep. 1, 2014, (Sep. 1, 2014), p. iv 268, XP055757959, NL, ISSN: 0923-7534, DOI: 10.1093/annonc/ mdu 336.25.
(Continued)

*Primary Examiner* — Robert A Sorey
*Assistant Examiner* — Kimberly A. Sass
(74) *Attorney, Agent, or Firm* — Snell & Wilmer LLP

(57) ABSTRACT

Methods, systems, and apparatus for a method that predicts an individual survival survival time of a patient. The method includes obtaining clinical data associated with health factors of the patient. The method includes obtaining liquid biopsy data associated with one or more attributes of diseased cells within the patient. The method includes predict-
(Continued)

ing or determining a survival time of the patient using a deep learning model based on the clinical data and the liquid biopsy data. The method includes providing or outputting the survival time.

15 Claims, 7 Drawing Sheets

(51) Int. Cl.
| | |
|---|---|
| *G16H 10/40* | (2018.01) |
| *G16H 10/60* | (2018.01) |
| *G16H 50/30* | (2018.01) |
| *G16H 50/70* | (2018.01) |
| *G06N 3/04* | (2006.01) |
| *G06N 3/08* | (2006.01) |
| *G16H 20/10* | (2018.01) |
| *G16H 20/70* | (2018.01) |
| *A61B 5/15* | (2006.01) |
| *A61B 10/02* | (2006.01) |
| *G06K 7/10* | (2006.01) |
| *G06K 19/07* | (2006.01) |

(52) U.S. Cl.
CPC ............ *G16H 10/60* (2018.01); *G16H 40/67* (2018.01); *G16H 50/30* (2018.01); *G16H 50/70* (2018.01); *A61B 5/15* (2013.01); *A61B 2010/0258* (2013.01); *G06K 7/10297* (2013.01); *G06K 19/0723* (2013.01); *G16H 20/10* (2018.01); *G16H 20/70* (2018.01)

(58) Field of Classification Search
CPC .......... G16H 20/10; G16H 20/70; G06N 3/04; G06N 3/08; A61B 5/15; A61B 2010/0258; G06K 7/10297; G06K 19/0723
See application file for complete search history.

(56) References Cited

U.S. PATENT DOCUMENTS

| | | |
|---|---|---|
| 2008/0064055 A1 | 3/2008 | Bryant et al. |
| 2009/0234627 A1 | 9/2009 | Yu et al. |
| 2011/0225112 A1* | 9/2011 | Cameron ............... G16H 50/50 706/20 |
| 2012/0009581 A1 | 1/2012 | Bankaitis-Davis et al. |
| 2015/0223759 A1 | 8/2015 | Ong et al. |
| 2016/0266127 A1 | 9/2016 | Kuhn et al. |

FOREIGN PATENT DOCUMENTS

| | | | | |
|---|---|---|---|---|
| WO | WO-2014151079 A2 * | 9/2014 | ....... | G01N 33/57411 |
| WO | WO-2015048740 A1 * | 4/2015 | ....... | G01N 33/57434 |
| WO | WO-2018147653 A1 * | 8/2018 | ............ | G06F 17/18 |

OTHER PUBLICATIONS

International Search Report and Written Opinion of the International Searching Authority (dated Aug. 14, 2018) for Corresponding International PCT Patent Application No. PCT/US2018/030013, filed Apr. 27, 2018.

* cited by examiner

SYSTEM AND METHOD FOR PREDICTING SURVIVAL TIME

CROSS-REFERENCE TO RELATED APPLICATIONS

This application claims priority to and the benefit of U.S. Provisional Patent Application No. 62/491,893 titled "SYSTEM AND METHOD FOR PREDICTING SURVIVAL TIME," filed on Apr. 28, 2017, and the entirety of which is hereby incorporated by reference herein.

BACKGROUND

Field

This specification relates to a system, method or apparatus for predicting survival time using deep learning.

Description of the Related Art

In a clinical setting, improvement of overall survival remains the ultimate treatment goal. Current standard of care relies on individual clinical features of a cancer patient (e.g., stage of the disease, subtype, previous treatments, etc.) to establish a population-based prognosis for the patient. For example, Cox Proportional Hazards models predict survival risks for patient cohorts not individual patients. Kaplan-Meier curves may be computed using population data after a clinical trial, for example, to gauge impact of treatment on patient survival. The overall survival Kaplan-Meier curves merely identify that a particular arm/cohort of patients in the clinical trial will likely do better than another arm of patients, and can lead to approval or dismissal of new treatment approaches (e.g., drugs or methods of treatment or the like). These curves are produced using population data, which are not meant to predict an outcome on an individual basis. Certain diagnostic approaches, such as single cell proteogenomics in liquid biopsies, can add specific value to the precision of the prognosis but typically fail on accuracy for an individual patient due to the high complexity of 'all data' that requires integration.

Currently, in addition to population-based survival curves, in order to determine a survival time for a particular patient, multiple data points of patient testing data may be recorded over time for the particular patient to generate a temporal survival trajectory. Monitoring may be used to track a patient's progress, but the data collected is not used to continuously update survival trajectories.

Accordingly, there is a need for improving the accuracy and precision of the prediction of the survival time on an individual basis of the patient that also accounts for the complexities involved in multiple treatments of the patient.

SUMMARY

In general, one aspect of the subject matter described in this specification may be embodied in a method for predicting a survival time of a patient. The method includes obtaining clinical data associated with health factors of the patient. The method includes obtaining liquid biopsy data associated with one or more attributes of diseased cells within the patient. The method includes predicting or determining a survival time of the patient using a deep learning model based on the clinical data and the liquid biopsy data. The method includes providing or outputting the survival time.

These and other embodiments may optionally include one or more of the following features. The clinical data may include an age, a sex or an ethnicity of the patient, patient blood data, electronic patient records, patient cancer advancement data or solid biopsy result data. The one or more attributes associated with the liquid biopsy data may correspond to enumeration data, such as an amount or number of diseased cells, or a morphologic representation of circulating or disseminating diseased cells, such as a shape of the diseased cells. The deep learning model may establish a relationship between the clinical data and the liquid biopsy data with the survival time of the patient. The deep learning model may be at least one of a feed-forward neural network, a convolutional neural network or a variational autoencoder. The survival time of the patient may indicate an amount of time that the patient has remaining to live due to the diseased cells within the patient. The liquid biopsy data may be from a single sample of blood and/or bone marrow aspirates of the patient.

Predicting or determining the survival time may be further based on the solid biopsy data. The method may include rendering on the display the survival time. The method may include obtaining the liquid biopsy data using a High-Definition Single-Cell Assay (HD-SCA) platform to detect the liquid biopsy data.

In another aspect, the subject matter may be embodied in a system for determining a survival time of a patient. The system includes a memory for storing clinical data that includes health factors of the patient and liquid biopsy data associated with one or more attributes of diseased cells within the patient. The system includes an output device configured to output the survival time of the patient. The system, includes a processor connected to the memory and the output device. The processor is configured to execute instructions stored in the memory. The processor performs operations that include obtaining the clinical data associated with the health factors of the patient. The operations include obtaining the liquid biopsy data associated with the one or more attributes of the diseased cells within the patient. The operations include predicting or determining a survival time of the patient using a deep learning model based on the clinical data and the liquid biopsy data. The operations include providing or outputting the survival time.

In another aspect, the subject matter may be embodied in a system for determining a survival time of a patient. The method includes an output device configured to output the survival time of the patient. The method includes a processor connected to the memory and the output device and configured to execute instructions stored in the memory. The processor is configured to obtain the clinical data associated with health factors of the patient. The processor is configured to obtain the liquid biopsy data including at least one of a number or a shape of the diseased cells within the patient. The processor is configured to predict or determining, by the processor, a survival time of the patient using a deep learning model based on the clinical data and the liquid biopsy data including the at least one of the number or the shape of the diseased cells. The processor is configured to provide or output the survival time.

BRIEF DESCRIPTION OF THE DRAWINGS

Other systems, methods, features, and advantages of the present invention will be apparent to one skilled in the art upon examination of the following figures and detailed description. Component parts shown in the drawings are not necessarily to scale, and may be exaggerated to better illustrate the important features of the present invention.

DETAILED DESCRIPTION

Disclosed herein are systems, apparatuses, devices and/or methods for a survivability prediction system ("prediction system") that predicts or determines survival time(s) of a patient for medical treatment. Particular embodiments of the subject matter described in this specification may be implemented to realize one or more of the following advantages. The prediction system predicts survival times for medical treatment. The prediction systems and methods described herein may be used in the context of clinical trials, to demonstrate an efficacy of a particular treatment. For example, if before a clinical trial of the particular treatment, if each individual patient participating in the trial has a specific survival prediction under certain confidence considerations, and after a short period of 21 days, if this survival predication has been extended by fifty percent (50%), an argument may be made to a governing regulatory body (e.g., the Food and Drug Administration) that there is a reason to use this as a surrogate endpoint.

Other benefits and advantages of the prediction system including predicting a survival time of a patient subjected to multiple treatments over time. Currently, in addition to population-based survival curves; in order to determine a survival time for a particular patient, multiple data points of patient testing data may be recorded over time for the particular patient to generate a temporal survival trajectory.

The prediction system accounts for many considerations and factors. Multiple treatments add complexity that involves careful consideration. This complexity is unable to be accounted for in a simple A vs. B test. Accordingly, survival time predictions determined using the prediction system may be updated whenever new data is obtained (e.g., when new liquid biopsy data is detected, as described herein), so that patient progress may be determined and appropriate adjustments to the patient treatment plan may be made. The updated predictions may also be used to approve new drugs in trials as a surrogate endpoint. Moreover, this allows for a manner in gauging treatment outcomes to determine whether a more aggressive treatment plan is needed or provide an early indication of the success or failure of an experimental treatment approach.

Additionally, the prediction system is able to determine the survival time for the patient at a given time using the data gathered regarding the patient prior to the given time (e.g., the clinical data and liquid biopsy data for the patient). When the survival time for the patient is capable of being determined at any given time, the doctors treating the patient are able to promptly determine a course of treatment.

Figure 1:
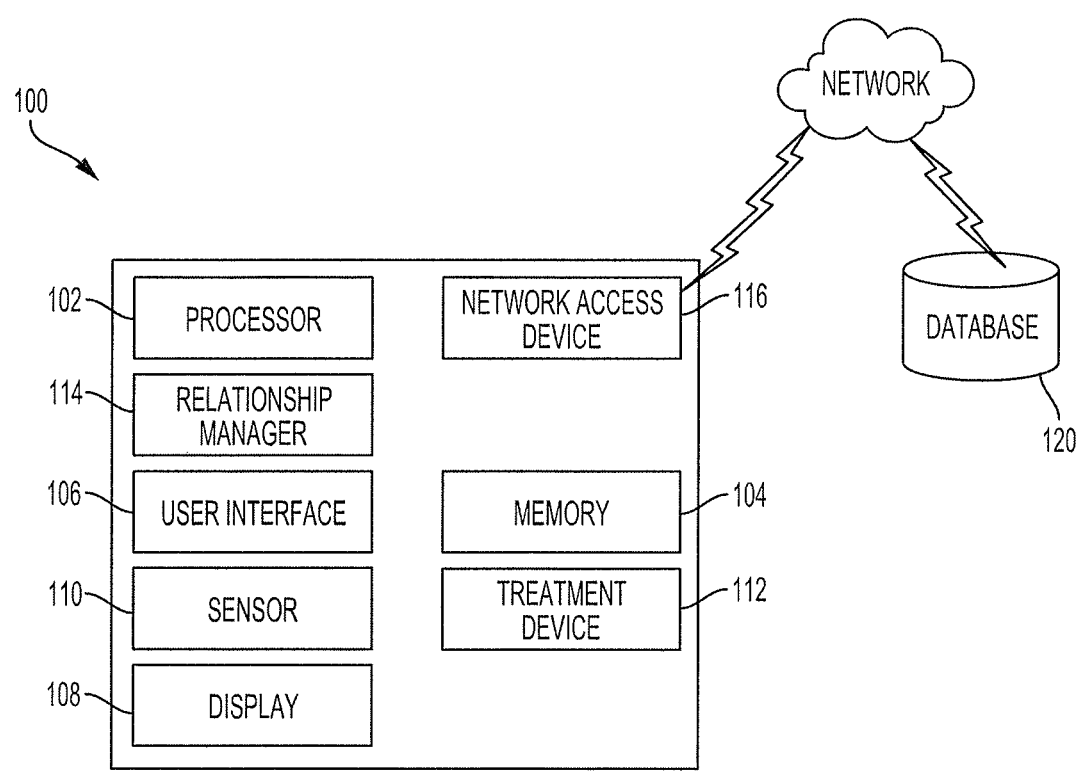
FIG. 1 is a block diagram of an example survivability prediction system according to an aspect of the invention.

FIG. 1 is a block diagram of an example survivability prediction system ("prediction system") 100. The prediction system 100 predicts or determines a survival time of a patient and is individualized for that patient. The survival time is the time that the patient has remaining to live until death. Conventional approaches to estimating the survival time of a patient rely on data collected from a group to estimate a survival time for the group having particular characteristics. Whereas, the prediction system 100 individualizes the prediction or determination of the survival time for the individual patient and may be determined using only a single point of data of the patient.

The prediction system 100 may administer a treatment, provide a recommendation for a treatment or communicate the survival time to the patient or attending physician once the survival time is predicted or determined. For example, the prediction system 100 may output the survival time or treatment recommendation on a display. This enhances and tailors the treatment to the individual patient.

The prediction system 100 includes a processor 102, a memory 104, a user interface 106 and an output device, such as a display 108. The prediction system 100 may include one or more sensors 110, a treatment device 112, a relationship manager 114 and/or a network access device 116. These components assist in the prediction and/or determination of the survival time and/or operate to provide treatment or recommendations to the patient, physician or other healthcare professional, based on the clinical data, the solid biopsy data and/or the liquid biopsy data obtained, detected and/or measured by the prediction system 100.

Clinical data of a patient or individual may indicate one or more characteristics or attributes of the health of the patient. For example, clinical data may include the weight, the height, the age, the gender, the socio-economic status, the diagnosis, the ethnicity or the race of the patient or other characteristics of the treatment, the disease or the patient. Other clinical data may include the stage of a disease, a subtype, and/or previous treatments. The clinical data may include data over a period of time and any relationships, changes or trends within the clinical data over the period of time. The prediction system 100 may use the treatment device 112 or the sensor 110 to detect or measure the clinical data. In some implementations, the prediction system 100 may obtain the clinical data through user input on the user interface 106 and/or from a database 120, e.g., via the network access device 116.

Liquid biopsy data may include blood or bone marrow draws from a patient, such as a metastatic prostate cancer patient, to detect, for example, the presence or the absence of circulating tumor cells (CTCs) in the blood. The liquid biopsy data may include a single blood sample or a bone marrow sample of the blood/bone marrow aspirates of the patient. The blood/bone marrow sample, for example, may indicate enumeration data, such as a number of tumor cells, or morphometric data, such as the shape of the tumor cells, flowing within the blood. The liquid biopsy data may be based on a High-Definition Single-Cell Assay (HD-SCA) liquid biopsy from metastatic prostate cancer patients, for example. The solid biopsy data may be taken directly from a tumor within a patient.

The HD-SCA platform looks for CTCs and disseminating tumor cells (DTCs) from the bone marrow aspirates. The use of the liquid biopsy is less invasive than a solid biopsy and less susceptible to complications. The enumeration data and morphometric parameters may also be detected and considered along with any clinical information available up to the time of blood and bone marrow aspirate draw. HD-SCA analysis results in images as well as tables of morphometric measurements of candidate cells, which may be displayed or provided to the patient or healthcare professional. Single cell genomics data and single cell proteomics data may also be, detected and used in the determination of survival time. The liquid biopsy data may include data over a period of time and any relationships, changes or trends within the liquid biopsy data over the period of time. Similarly, the solid biopsy data may include data over a period of time and any relationships, changes or trends within the solid biopsy data over the period of time.

The prediction system 100 includes a processor 102. The processor 102 may include one or more data processing apparatuses, such as a controller or a computer. The processor 102 may access the memory 104 to perform programmed instructions stored on the memory 104. The processor 102 executes the programmed instructions to determine or predict the survival time of the patient, train the deep learning survivability model ("deep learning model"), and/or operate the treatment device 112 or output device to administer treatment, recommend a course of treatment and/or provide, display or otherwise output the survival time to the patient or healthcare professional. The processor 102 may perform other functions, such as measuring and/or detecting diseased cells flowing within the blood of the patient or obtain other data, such as the clinical data, the solid biopsy data and/or the liquid biopsy data, from another device, such as the sensor 110 or the database 120, to facilitate the prediction or determination of the survival time of the patient.

The memory 104 may be coupled to the processor 102. The memory 104 may store instructions to execute on the processor 102 and may include a computer-readable medium, such as one or more of a RAM or other volatile or non-volatile memory. The memory 104 may be a non-transitory memory or a data storage device, such as a hard disk drive, a solid-state disk drive, a hybrid disk drive, or other appropriate data storage, and may further store machine-readable instructions, which may be loaded and executed by the processor 102. The memory 104 may store, for example, obtained clinical data, solid biopsy data and liquid biopsy data that are further processed by the processor 102 to predict the survival time, output or display the information, formulate and provide a recommendation and/or administer treatment. The memory 104 may have an internal database that stores the clinical data, the solid biopsy data and/or the liquid biopsy data for multiple patients and/or a population of patients.

In some implementations, the prediction system 100 may include a network access device 116 to access an external database 120 across a network 118 to obtain the clinical data, the solid biopsy data and/or the liquid biopsy data, for example. The network access device 116 may include a communication port or channel, such as one or more of a Wi-Fi unit, a Bluetooth® unit, a radio frequency identification (RFID) tag or reader, or a cellular network unit for accessing a cellular network (such as 3G or 4G). The network access device 116 may transmit data to and receive data from devices and systems not directly connected to the prediction system 100, such as the external database 120 across the network 118.

The network 118, such as a local area network (LAN), a wide area network (WAN), a cellular network, the Internet, or combination thereof, connects the prediction system 100 to the one or more external databases 120. The external database 120 may include many databases from different service providers, hosts or other health and/or data institutions, such as the National Institute of Health. A service provider may provide information, such as the clinical data, the solid biopsy data and/or the liquid biopsy data of a population, to the prediction system 100.

A database is a collection of information that is organized for search and retrieval, such as by a computer, and the database may be organized in tables, schemas, queries, reports, or any other data structures. A database may use any number of database management systems. The database may include a third-party server or website that stores or provides information. The information may include real-time information, periodically updated information, or user-inputted information. A server may be a computer in a network that is used to provide services, such as accessing files or sharing peripherals, to other computers in the network. A website may be a collection of one or more resources associated with a domain name.

The prediction system 100 may include a user interface 106 or other input/output device. The user interface 106 is a device capable of receiving user input, such as a keyboard, a touch screen, a microphone, and/or a button, and/or providing output, such as a display and/or a speaker. The prediction system 100 may use the user interface 106 to receive user input including the clinical data, the solid biopsy data and/or the liquid biopsy data, for example, or provide output including the survival time(s), treatment(s) and/or recommendation(s), for example, to the patient or healthcare professional. The prediction system 100 may use another output device, such as the display 108, that performs some of the output functions, such as the display of the survival time. The user interface 106 allows the patient or healthcare professional to input information, such as the clinical data, the solid biopsy data or the liquid biopsy data.

The prediction system 100 may include an output device, such as the display 108, that is different or the same as the user interface 106. The prediction system 100 may use the output device to provide information, such as a recommended course of treatment and/or a survival time to the patient and/or healthcare professional. The display 108 may be a liquid crystal display (LCD), a projection or a projector, a computer or laptop screen, a smartphone screen or other display device. In some implementations, the output device may be a printer or other print device that presents the information in a physical format. The output device may be a remote device or a local device.

The prediction system 100 may include one or more sensors 110. The one or more sensors 110 may measure and/or detect aspects of the clinical data, the solid biopsy data and/or the liquid biopsy data and provide the measured and/or detected data to the processor 102. For example, the one or more sensors 110 may measure the amount or number of diseased cells, such as cancer cells, within the blood/bone marrow of the patient and/or detect the shape of the diseased cells.

The prediction system 100 may include a relationship manager 114. In some implementations, the processor 102 may perform the functions of the relationship manager 114. The relationship manager 114 associates a predicted or determined survival time of the patient to a treatment. For example, the relationship manager 114 may identify that an increased survival time is associated with a new drug being taken by the patient, and thus, the relationship manager 114 identifies that using the new drug (or combinations of new drugs and specific doses for each drug) results in a longer life expectancy for the patient. In another example, the relationship manager 114 may identify a course of treatment that the patient should undertake to increase the patient's life expectancy based on the survival time. That is, the relationship manager 114 may identify a proactive course of treatment and/or the success or failure of a current course of treatment.

The relationship manager 114 interpolates and/or predicts the effects of a course of treatment and/or the causes of an increased or decreased survival time of the patient to improve the likelihood of success of a course of treatment and increase the survival time of the patient. The relationship manager 114 does more than just prescribe the correct dosage based on the survival time, the relationship manager 114 predicts and/or interpolates the causal relationship of adjusting and/or modifying the course of treatment on the patient on an individual basis based on the patient's specific history and reactions to a previously-prescribed treatment. This tailors the effects of the treatment to the individual to allow for a more accurate and precise determination of causal relationships so that an individualized course of treatment may be developed, measured and/or administered.

The prediction system 100 may include a treatment device 112, such as a medical device, to administer or provide the treatment. The prediction system 100 may control the treatment device 112 to administer the correct treatment, such as a prescribed medicine or procedure. The treatment device 112 may provide various recommendations including medical and lifestyle changes as a course of treatment.

Figure 2:
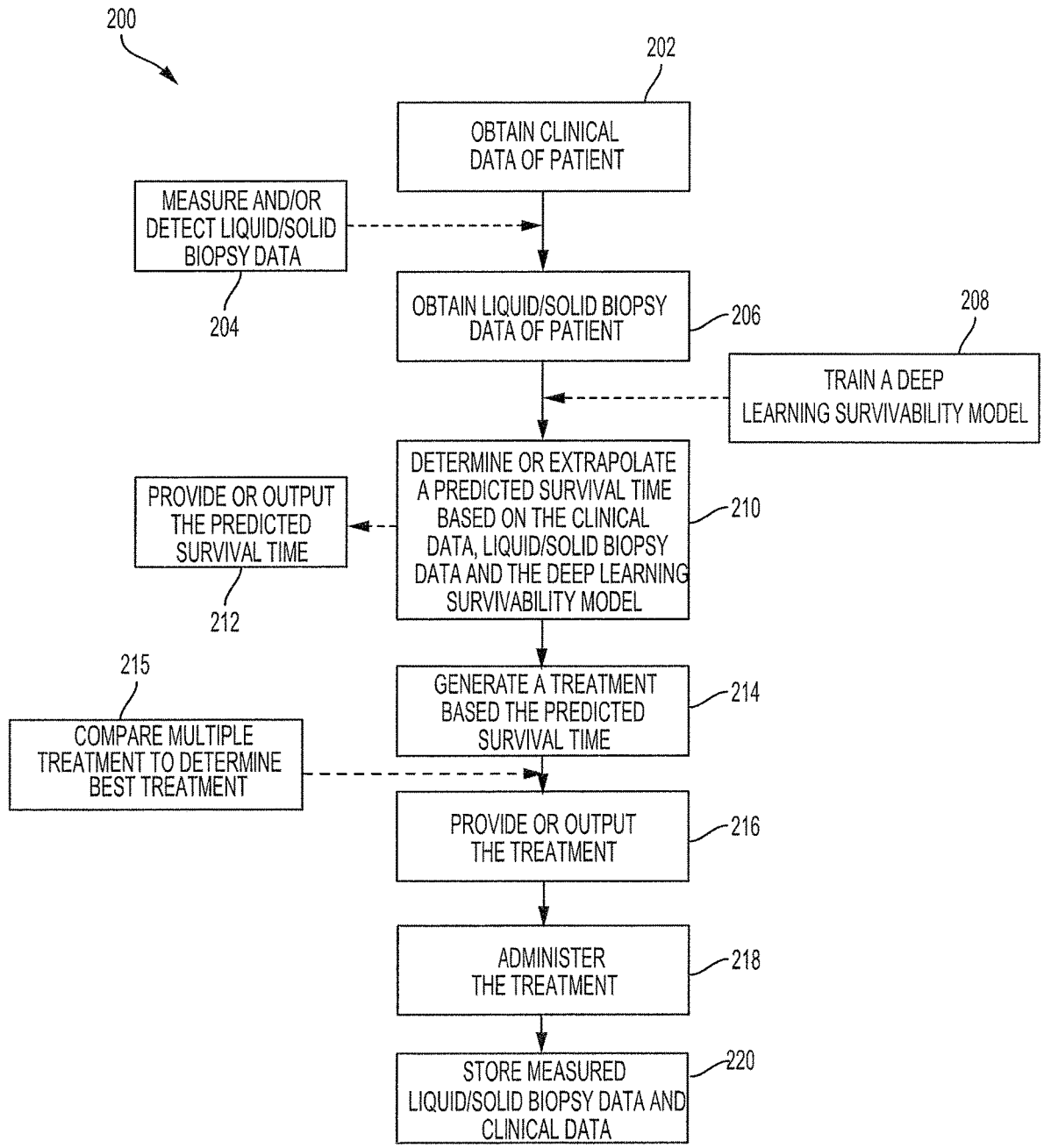
FIG. 2 is a flow diagram of an example process for providing or outputting a treatment based on the survival time using the prediction system of FIG. 1 according to an aspect of the invention.

FIG. 2 describes the process 200 for providing or outputting a treatment based on the survival time. One or more computers or one or more data processing apparatuses, for example, the processor 102 or the relationship manager 114 of the prediction system 100 of FIG. 1, appropriately programmed, may implement the process 200.

The prediction system 100 obtains clinical data of the patient (202). The prediction system 100 may obtain the clinical data from the memory 104. The memory 104 may store clinical data for many patients. The prediction system 100 may identify the patient based on user input through the user interface 106 or using one or more sensors 110 to detect the identity of the patient. The prediction system 100 may access the memory 104 and associate the identity of the patient with a set of clinical data associated with the patient and obtain the clinical data associated with the patient. In some implementations, the prediction system 100 establishes a communication with the database 120 using the network access device 116, provides an identity of the patient to the database 120, and obtains the clinical data.

In some implementations, one or more sensors 110 may measure and/or detect the clinical data of the patient to obtain the clinical data of the patient. For example, a weight sensor may measure the weight of the patient and provide the weight to the processor 102.

The prediction system 100 may use one or more sensors 110 to measure and/or detect the liquid biopsy data and/or the solid biopsy data (204). The one or more sensors 110 may detect the presence or absence of diseased cells, such as CTCs, and/or measure the amount or number of diseased cells within the blood and/or bone marrow of the patient. In some implementations, the one or more sensors 110 may detect the shape of the diseased cells.

The prediction system 100 obtains liquid biopsy data and/or solid biopsy data of the patient (206). Similar to the clinical data, the prediction system 100 may obtain the solid biopsy data and/or the liquid biopsy data of the patient from various sources including the memory 104, a database 120 and/or from the one or more sensors 110. The database 120 may be remote or local, for example, and connected via the network 118 using the network access device 116. In some implementations, the prediction system 100 may obtain the solid biopsy data and/or the liquid biopsy data from user input via the user interface 106. The clinical data, the solid biopsy data and/or the liquid biopsy data may be obtained from the same or different locations. The clinical data, the solid biopsy data and/or the liquid biopsy data may be a single sample or draw of a single patient. The prediction system 100 may only need the single sample or draw to predict the survival time. This minimizes the number of samples, number of draws or amount of data needed to predict the survival time, which reduces cost and time. In some implementations, the prediction system 100 may obtain the solid biopsy data. The prediction system 100 may obtain the solid biopsy in addition to and/or in combination with the liquid biopsy data and/or clinical data.

Figure 3:
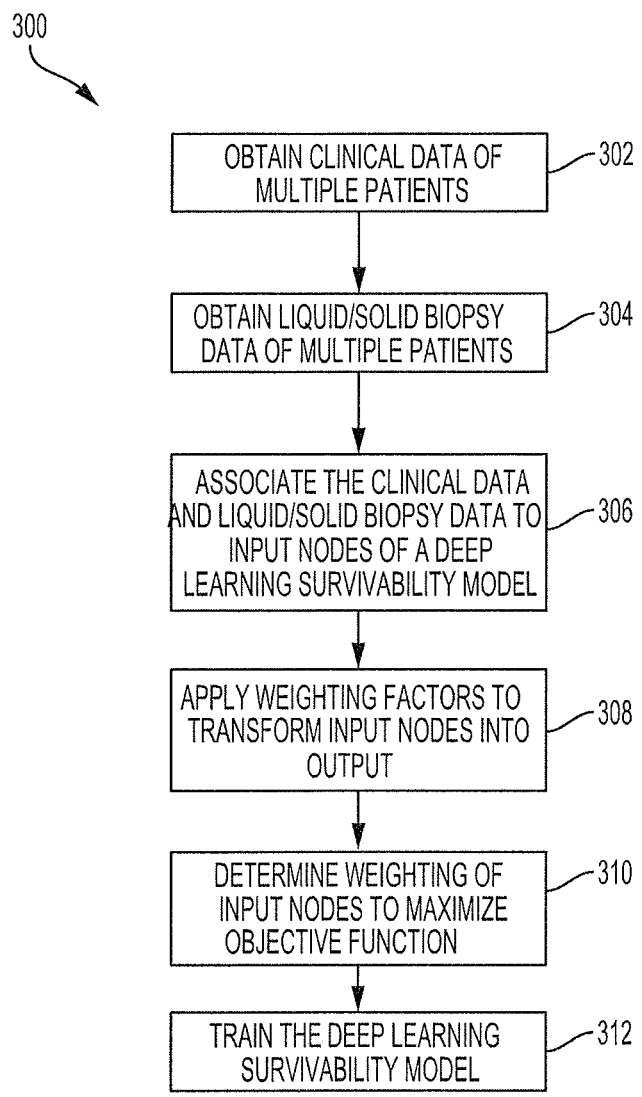
FIG. 3 is a flow diagram of an example process for training a deep learning survivability model used to predict or determine the survival time using the prediction system of FIG. 1 according to an aspect of the invention.

The prediction system 100 may train a deep learning survivability model ("deep learning model") that is used to extrapolate, predict or otherwise determine the survival time of the patient based on the obtained the liquid biopsy data, the solid biopsy data and/or the clinical data (208). FIG. 3 further describes the process 300 for training the deep learning model.

Figure 4:
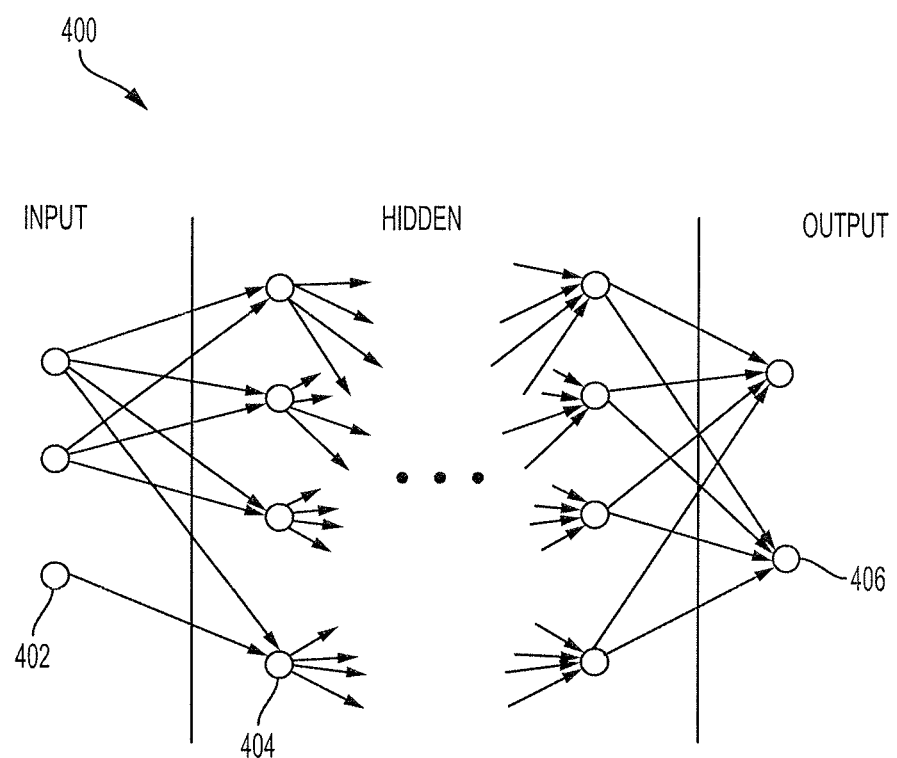
FIG. 4 shows an example graph deep learning survivability model used by the prediction system of FIG. 1 according to an aspect of the invention.

The prediction system 100 determines, predicts or extrapolates a survival time based on the clinical data, the solid biopsy data and/or the liquid biopsy data (210). The prediction system 100 may use a deep learning model on the clinical data, the solid biopsy data and/or the liquid biopsy data to determine or predict the survival time. The deep learning model may have multiple layers of nodes, which include multiple input nodes 402, hidden nodes 404 and/or output nodes 406, as shown in FIG. 4 for example. The deep learning model may be at least one of a fully connected or feed-forward neural network, a convolutional neural network or a variational autoencoder.

In order to determine, predict or extrapolate the survival time, the prediction system 100 may associate each input node of the deep learning model to the clinical data, the solid biopsy data and/or the liquid biopsy data of the specific patient to provide an individualized survival time for the specific patient, as an output. Each input node may have the same data that includes a totality of the clinical data, the solid biopsy data and/or the liquid biopsy data. The prediction system 100 may predict a survival time for the specific patient based on the patient's own clinical data, solid biopsy data and/or liquid biopsy data. This allows the prediction system 100 to input a single data point of the specific patient and use the deep learning model to extrapolate, predict or otherwise determine the survival time that is unique to the specific patient.

The prediction system 100 uses multiple layers of hidden nodes to transform each input node into an output node. At each layer of the hidden nodes, the prediction system 100 applies a nonlinear transformation for each input into the next layer. The nonlinear transformation may be a weighted aggregation of each input. Each input may be weighted differently and then aggregated. Each output of a previous layer is weighted then aggregated to form the input to the next layer so that a subsequent layer is a transformation of the previous layer. The prediction system 100 may use different nonlinear functions for the nonlinear transformation between different layers of nodes.

The first layer of hidden nodes is a transformation of the input nodes, the second layer of hidden nodes is a transformation of the first layer of hidden nodes, and the third layer of hidden nodes is a transformation of the second layer of hidden nodes, etc., for example. The output nodes are a transformation of the previous layer of hidden nodes, for example.

In response to the prediction or determination of the survival time, the prediction system 100 may provide or output the survival time to the patient and/or the healthcare professional (212). For example, the prediction system 100 may render the survival time on the display 108. In another example, the prediction system 100 may output the survival time via a different output device, such as electronically sending the survival time to another electronic device or application for processing or use. In another example, the prediction system 100 may print out the survival time, such as in a lab report.

The prediction system 100 may generate a treatment based on the survival time (214). The prediction system 100 may use the relationship manager 114 or processor 102 of the prediction system 100 to associate at least one of the survival time, the solid biopsy data, the liquid biopsy data or the clinical data with a disease or a stage of the disease and recommend a more or less aggressive course of treatment based on the association. The database of the associations may be stored in the memory 104. The prediction system 100 may generate the treatment based on the changes in the survival time and the changes in the clinical data, the solid biopsy data and/or the liquid biopsy data over a period of time for the individual patient.

For example, if the liquid biopsy data indicates a greater number of diseased cells at a second point of time than at a first point of time that came beforehand and the survival time indicates that the patient has less time to live, the relationship manager 114 may associate the advanced state of the disease with a greater dosage of the current medication or recommend an alternative medication. In another example, if the clinical data indicates that the patient is improving and the survival time of the patient is increasing, the relationship manager 114 may determine that the current treatment is effective and/or recommend a reduced dosage of the current treatment. In another example, if the survival time becomes normalized to that of a healthy patient, the relationship manager 114 may determine that the current treatment may end. By altering the treatment based on the historical changes to the individual patient, the prediction system 100 improves the accuracy of generation of the treatment for the individual patient that is specific to the patient's survivability.

The prediction system 100 may compare multiple different survival times of the same patient with the same diagnosis but applying different treatments or course of treatments to determine the best treatment (215). By comparing different survival times that results from different treatments or course of treatments, the prediction system 100 may illustrate to the patient and/or healthcare professional the predicted benefits of one treatment over another. The best treatment may be the treatment with the greatest survival time. In some implementations, the best treatment may be the treatment with the lowest cost, while providing a reasonable survival time. For example, the prediction system 100 determines or predicts the survival time for the patient using a first treatment as an input to the deep learning model, and then using a second treatment as an input to the deep learning model. The prediction system 100 compares the two results and may calculate a difference in the survival times based on the two results that show the advantages of one treatment over another. The prediction system 100 outputs or provides the differences in the cause-and-effect of the two different treatments so that a more advantageous course of treatment may be followed, instead of relying on a reactive analysis of a course of treatment to determine the success or failure of the course of treatment.

The prediction system 100 may provide or output the treatment to the patient and/or the healthcare professional (216). The prediction system 100 may use the output device, e.g., the display 108, to provide or output the treatment. For example, the prediction system 100 may render a description of the recommended treatment on the display 108 and/or print out the recommended treatment. The treatment may be based on the survival time.

The prediction system 100 may administer the treatment (218). The prediction system 100 may use the treatment device 112 to administer an amount of medication or treatment to the patient. The amount of medication or treatment may be based on the recommended treatment. For example, if the recommended treatment is to increase the dosage of a current medication based on the survival time, the solid biopsy data, the liquid biopsy data and/or the clinical data, the prediction system 100 adjusts the amount of current medication and/or adjusts the treatment to the patient.

The prediction system 100 may store the liquid biopsy data, the solid biopsy data and/or the clinical data into the memory 104 or the database 120 along with an association with the survival time (220). The prediction system 100 may store the liquid biopsy data, the solid biopsy data and the clinical data in conjunction with an associated survival time that results at the same time that the liquid biopsy data, the solid biopsy data and the clinical data are taken to analyze the effects to the patient over time. The prediction system 100 may use the stored liquid biopsy data, the solid biopsy data and/or the clinical data to update the survival time of the patient, as the treatment of the patient progresses. This allows the prediction system 100 to account for changes in the collected clinical data, the solid biopsy data and/or the liquid biopsy data over a period of time. The prediction system 100 may provide up-to-date recommendations and predictions of the progression of the patient, as the treatment is being received, based on the timing of treatments and the corresponding changes to the patient reflected in the liquid biopsy data, the solid biopsy data and/or the clinical data, which cause a change in the survival time. By having the historical information of the liquid biopsy data, the solid biopsy data and/or the clinical data and updating the survival time accordingly over the period of time, the prediction system 100 may monitor the effectiveness of the treatment, and provide immediate adjustments, changes or recommendations for the course of treatment to the patient.

FIG. 3 describes the process 300 for training the deep learning model used to predict the survival time of the patient. One or more computers or one or more data processing apparatuses, for example, the processor 102 of the prediction system 100 of FIG. 1, appropriately programmed, may implement the process 300.

The deep learning model is capable of integrating heterogeneous data types better than the statistical model. The deep learning model is able to extract meaningful representations from these heterogeneous data types, leading to accurate predictions. Neural networks, particularly recurrent neural networks, are able to capture long term interactions. That is, neural networks are able to accurately predict interactions at a particular time point based on data from a previous time point. The deep learning models may be able to determine a survival time based on a single data point of the liquid biopsy data, the solid biopsy data and/or the clinical data. Using this immediate determination, clinicians can more promptly decide how aggressive of a treatment to implement. Further advantages of utilizing the deep learning model are described in FIGS. 5A-8.

The deep learning model 400 has one or more input nodes 402, one or more hidden nodes 404 and one or more output nodes 406, as shown in FIG. 4 for example. The one or more input nodes 402 may represent attributes of the clinical data, such as age, sex, ethnicity or other attributes of a patient, and attributes of the liquid biopsy data, such as a number or shape of the diseased cells within the patient. The deep learning model 400 may have one or more layers of hidden nodes.

The prediction system 100 obtains the clinical data of multiple patients or a population as an input (302). The prediction system may obtain the clinical data through various means, such as user input through the user interface 106, from a database 120 or from the memory 104. For example, the prediction system 100 may communicate with and access the memory 104, communicate with and access the database 120 using the network access device 116 through the network 118, and/or receive user input through the user interface 106 to obtain the clinical data as the input. The prediction system 100 may use a similar manner to obtain the liquid biopsy data and/or the solid biopsy data of the multiple patients or the population of patients using the memory 104, the database 120 or the user interface 106, as described above for the clinical data (304).

The prediction system 100 associates the clinical data, the solid biopsy data and the liquid biopsy data to one or more input nodes of a deep learning model (306). The prediction system 100 may apply various different weighting factors to each input node of the one or more input nodes to transform the clinical data, the solid biopsy data and the liquid biopsy data to an outcome node that corresponds to a solution of the objective function (308). The prediction system 100 may use multiple layers of hidden nodes to perform the transformation. The transformation may be a nonlinear transformation at each layer.

The objective function may correspond to the survival time of the patient and/or concordance index. In some implementation, the objective function may include the accuracy and precision of the survival time of the patient relative to the ground truth (or the actual survival time of the patient).

For example, the prediction system 100 calculates the survival time using a first combination of the various different weighting factors and calculates the survival time using a second combination of the various different weighting factors. The prediction system 100 formulates the survival time using any number of combinations of weighting factors and any number of layers of hidden nodes where the transformation of the inputs occur. In each layer of hidden nodes, the prediction system 100 applies a different combination of weighting factors to the input into the layer of hidden nodes. The weighting factors may be initialized randomly.

The prediction system 100 formulates an output node based on the combination of weighting factors in each layer of nodes and each transformation to form the objective function. The prediction system 100 applies the different combination of weighting factors within the different layers.

The prediction system 100 maximizes the objective function to determine the final weighting of the nodes in each layer to be used in transforming the one or more nodes of one layer to the one or more nodes in a subsequent layer (310). The prediction system 100 may select the combination of weighting factors in each layer that maximizes the objective function to determine the final weighting at each layer. The prediction system 100 trains the deep learning model to determine the final weights of the deep learning model, which are used in the prediction of the survival time.

Figure 5A:
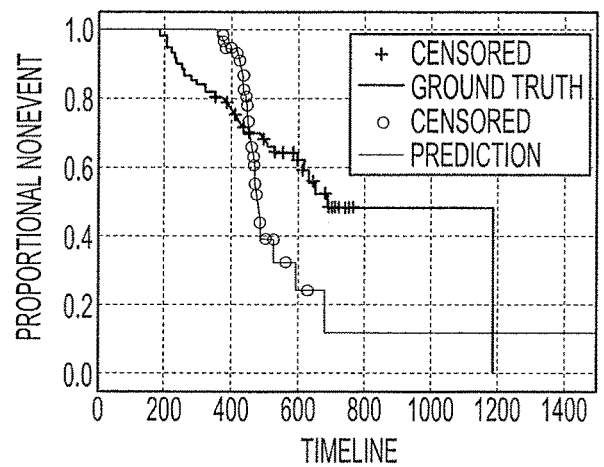
FIGS. 5A-5C show example graphs of overall survival curves from the prediction system of FIG. 1 using a deep learning model according to an aspect of the invention.
Figure 5B:
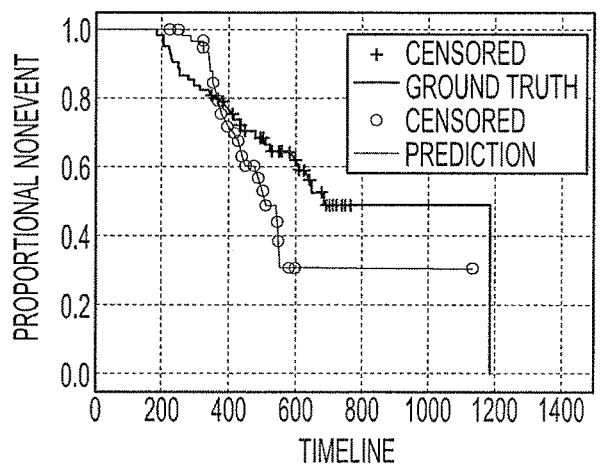
Figure 5C:
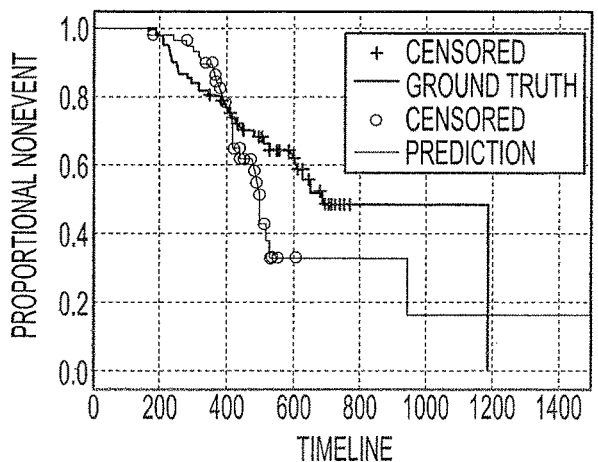

FIGS. 5A-5C shows graphs of Kaplan-Meier Curves using the deep learning model with clinical and liquid biopsy data for the prediction of overall survival (OS) time. For example, FIG. 5A shows the deep learning model relying solely on clinical data to predict the overall survival time. FIG. 5B shows the deep learning model using both clinical data and morphometric data (shape of the diseased cells) of the liquid biopsy data to predict the survival time. FIG. 5C shows the deep learning model using the clinical data, the morphometric data of the liquid biopsy data and the enumeration data (number of diseased cells). As shown in FIGS. 5A-5C, the inclusion of the liquid biopsy data improves the accuracy and precision of the predicted survival time relative to the ground truth (or actual survival time of the patient). The deep learning model becomes more accurate and precise when morphometric and enumeration data of the liquid biopsy data is incorporated. That is, the overall survival time predictions are better and closer to the ground truth when the liquid biopsy data is incorporated.

Figure 6A:
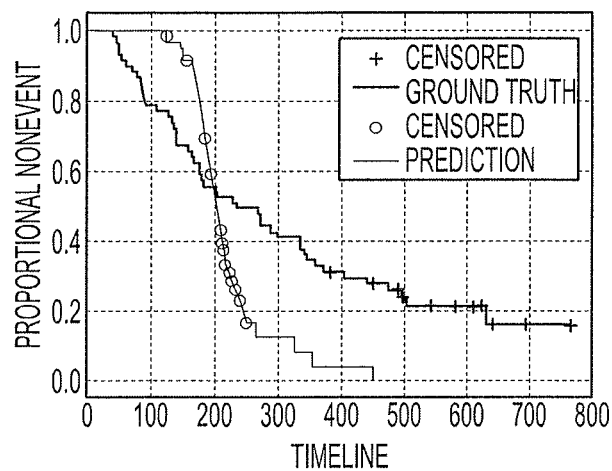
FIGS. 6A-6C show example graphs of progression free survival curves from the prediction system of FIG. 1 using the deep learning model according to an aspect of the invention.
Figure 6B:
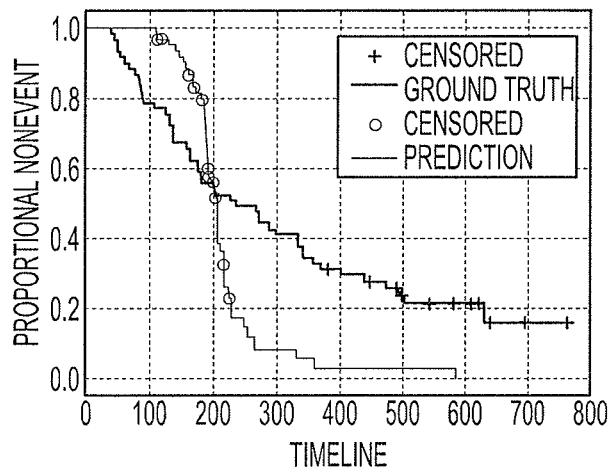
Figure 6C:
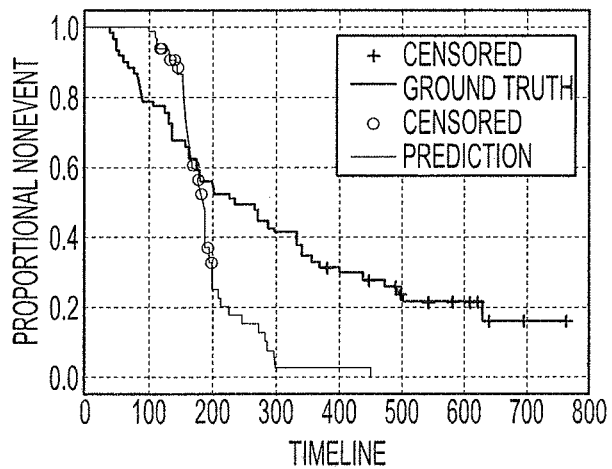

FIGS. 6A-6C show graphs of Kaplan-Meier Curves using the deep learning model with clinical and liquid biopsy data for the prediction of progression free survival (PFS) time. The PFS time occurs when the patient has not switched treatments. For example, FIG. 6A shows the deep learning model relying solely on clinical data to predict the PFS time. FIG. 6B shows the deep learning model using both clinical data and morphometric data of the liquid biopsy data to predict the PFS time. FIG. 6C shows the deep learning model using the clinical data, the morphometric data of the liquid biopsy data and the enumeration data. As shown in FIGS. 6A-6C the inclusion of the liquid biopsy data improves the accuracy and precision of the predicted survival time relative to the ground truth. The deep learning model becomes more accurate and precise when morphometric and enumeration data of the liquid biopsy data is incorporated. Similarly, the progression free survival time predictions are better and closer to the ground truth when the liquid biopsy data is incorporated.

Figure 7:
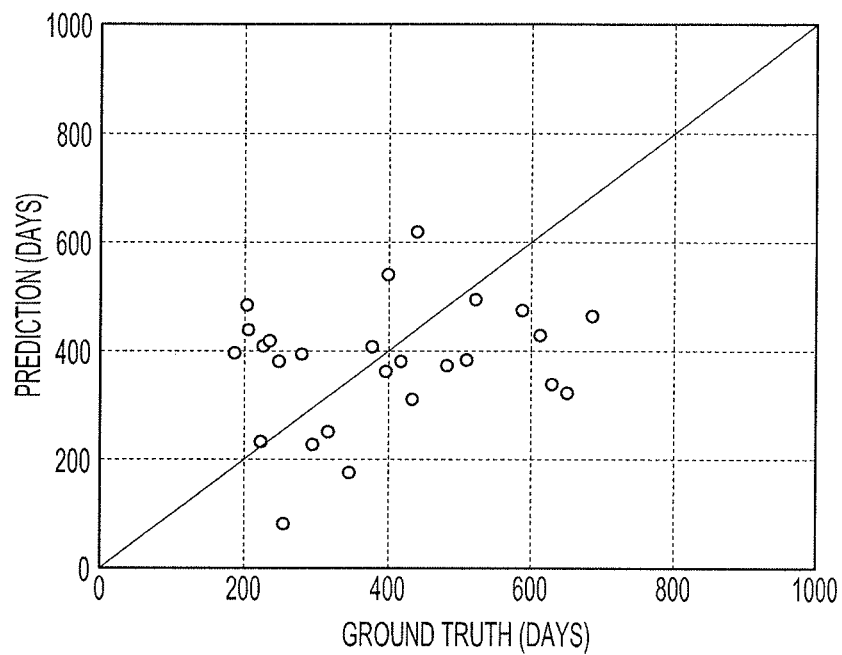
FIG. 7 shows an example graph of the linear correlation between the ground truth and the predicted overall survival time from the prediction system of FIG. 1 according to an aspect of the invention.

FIG. 7 shows a graph of the linear correlation between the ground truth and prediction of the survival time from the deep learning model for the overall survival time prediction. The graph shows that the predicted survival time from the deep learning model is highly correlated with the actual ground truth.

Figure 8:
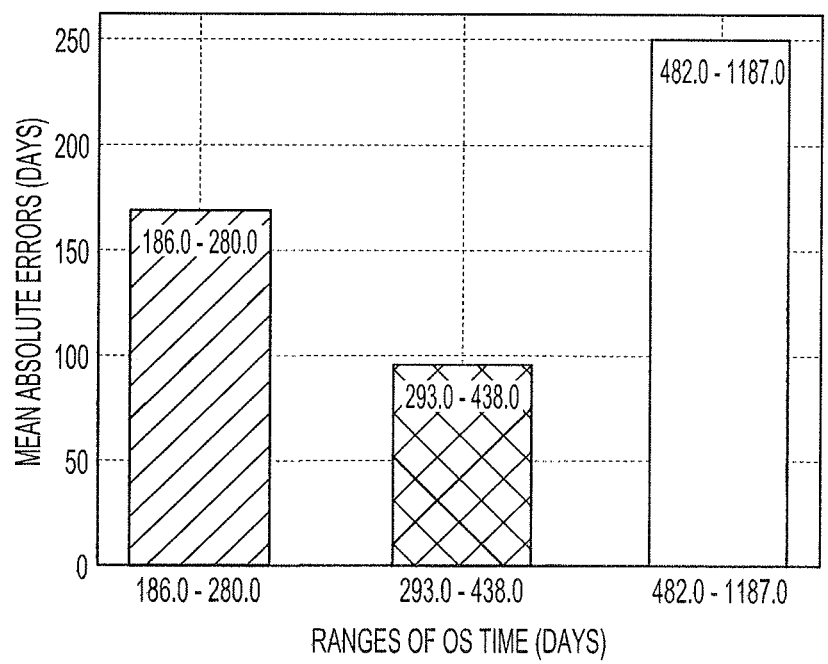
FIG. 8 shows an example graph of the early and late death prediction errors of the predicted overall survival time from the prediction system of FIG. 1 in comparison to the ground truth according to an aspect of the invention.

FIG. 8 shows a graph of the early and late death prediction errors of the predicted survival time from the deep learning model in comparison to the ground truth. The deep learning model may provide for a more accurate prediction of the overall survival time when the actual ground truth survival time of the patient is approximately 293-438 days in comparison to later or earlier actual ground truth survival times. Moreover, the deep learning model is more accurate in predicting earlier actual ground truth survival times than later actual ground truth survival times. Late death prediction errors from the deep learning model are nearly 1.5 times greater than the early death prediction errors.

Exemplary embodiments of the invention have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. A method for providing treatment based on at least prediction data of patient survival time in accordance with a dosage amount and recommended treatment for improvement of patient treatment response, comprising:
controlling, by at least one processor, a treatment device based on clinical data associated with a patient by:
implementing, by the at least one processor, a prediction unit that uses a neural network for predicting at least a patient survival time based on one or more comparisons of the clinical data associated with the patient with overall clinical data wherein the neural network is configured to associate one or more input nodes with at least the clinical data and a biopsy data associated with the patient, and with the overall clinical data to provide an output of data of at least the patient survival time wherein the prediction unit is configured to:
input a single data point associated with the patient to an input node of the neural network to determine a survival time specific to the patient; and
receive output of treatment data from a deep learning model of the neural network based on the survival time specific to the patient in accordance with at least a stage of a disease that is specific to the patient based on the clinical data and the biopsy data comprising solid biopsy data associated with the patient;
in response to output of the treatment data from the neural network, adjusting, by the at least one processor, a dosage of treatment administered by the treatment device to the patient and sending a recommendation of a change of the treatment based on the treatment data from the deep learning model; and
rendering, by a display device that is communicatively coupled to the at least one processor, a description generated by the at least one processor of a recommended treatment based on the survival time specific to the patient and outputted from the deep learning model of the neural network based on the clinical data and the biopsy data associated with the patient.

2. The method of claim 1, wherein the biopsy data further comprises liquid biopsy data that is from a single draw of blood and/or bone marrow aspirates of the patient; and wherein the description generated by the at least one processor of a recommended treatment comprises an up-to-date recommendation that includes a description of a progression of the patient as the treatment is received based on at least a timing of the treatment and any corresponding changes that are determined by the deep learning model reflected in at least the clinical data associated with the patient.

3. The method of claim 1, wherein predicting or determining the survival time is further based on solid biopsy data.

4. The method of claim 3, further comprising rendering, on the display device, the survival time.

5. The method of claim 1, wherein the deep learning model is at least one of a convolutional neural network or a variational autoencoder.

6. The method of claim 2, wherein obtaining the liquid biopsy data includes using a High-Definition Single-Cell Assay (HD-SCA) platform to detect the liquid biopsy data.

7. A system for determining a survival time of a patient, comprising:
a memory for storing clinical data that includes health factors of the patient and liquid biopsy data associated with one or more morphologic attributes of diseased cells within the patient, the one or more attributes associated with the liquid biopsy data corresponding to a morphologic representation of circulating or disseminating diseased cells including an amount or number of diseased cells or a shape of the diseased cells;
a treatment device for administering or providing a treatment or a recommendation of the treatment;
one or more processors connected to the memory and the treatment device, and configured to execute instructions stored in the memory, the one or more processors performing a set of operations comprising:
obtaining, from the memory, the clinical data associated with the health factors of the patient,
obtaining, from the memory, the liquid biopsy data associated with the one or more attributes of the diseased cells within the patient,
predicting or determining, by the one or more processors, the survival time of the patient using a deep learning model based on a combination of the clinical data and the liquid biopsy data, wherein the deep learning model is executed by the processor to establish a relationship between the clinical data and the liquid biopsy data with the survival time of the patient, wherein the survival time of the patient indicates an amount of time that the patient has remaining to live due to the diseased cells within the patient wherein the amount of time that the patient has remaining is based on a single data point associated with the patient input to the deep learning model to determine a survival time specific to the patient,
operating, by the one or more processors, the treatment device to administer the treatment or provide the recommendation of the treatment to the patient based on the survival time predicted or determined by the deep learning model specific to the patient, and
displaying, by a display device coupled to the one or more processors, the treatment or the recommendation of the treatment to the patient based on the survival time predicted or determined by the deep learning model wherein the recommendation comprises a set of recommendations based on a recommendation of a progression of the patient, a recommendation that is generated as the treatment is received, a recommendation based on a timing of treatment and a corresponding change to the patient reflected in the at least one of the liquid biopsy data, a solid biopsy data, and the clinical data which is associated with a change in the survival time of the patient.

8. The system of claim 7, wherein the clinical data includes an age, sex or ethnicity of the patient, one or more of patient blood data, patient cancer advancement data, or solid biopsy result data.

9. The system of claim 7, wherein the liquid biopsy data is from a single sample of blood and/or bone marrow aspirates of the patient.

10. The system of claim 7, wherein predicting or determining the survival time is further based on solid biopsy data.

11. The system of claim 7, wherein the processor is further configured to render, on a display, the survival time.

12. The system of claim 7, wherein the deep learning model is at least one of a convolutional neural network or a variational autoencoder.

13. A system for determining survival time of a patient, comprising:
   an output device configured to output the survival time of the patient; and
   a processor connected to the memory and the output device and configured to execute instructions stored in the memory, the processor being configured to:
      obtain a clinical data associated with health factors of the patient,
      obtain a liquid biopsy data including at least one of a number or shape of the diseased cells within the patient,
      predict or determining a survival time of the patient using a deep learning model based on the clinical data and the liquid biopsy data including the at least one of the number or shape of the diseased cells, wherein the deep learning model is executed by the processor to establish a relationship between the clinical data and the liquid biopsy data with the survival time of the patient, wherein the survival time of the patient indicates an amount of time that the patient has remaining to live due to the diseased cells within the patient wherein the amount of time that the patient has remaining is based on a single data point associated with the patient input to the deep learning model to determine a survival time specific to the patient, and
      provide or output, using the output device, the survival time specific to the patient wherein the output device comprises at least a display device to display a treatment or the recommendation of the treatment to the patient based on the survival time predicted or determined by the deep learning model wherein the recommendation comprises a set of recommendations based on a recommendation of a progression of the patient, a recommendation that is generated as the treatment is received, a recommendation based on a timing of treatment and a corresponding change to the patient reflected in at least one of the liquid biopsy data, a solid biopsy data, and the clinical data which is associated with a change in the survival time of the patient.

14. The system of claim 13, wherein to obtain the liquid biopsy data the processor is configured to use a High-Definition Single-Cell Assay (HD-SCA) platform to detect the liquid biopsy data.

15. The system of claim 13, further comprising:
   a treatment device for administering or providing a treatment or a recommendation of the treatment, wherein the processor is configured to operate the treatment device to administer the treatment or provide the recommendation of the treatment to the patient based on the predicted or determined survival time.

* * * * *